(12) United States Patent
Hibara et al.

(10) Patent No.: US 9,719,927 B2
(45) Date of Patent: Aug. 1, 2017

(54) LIGHT POLARIZATION ANALYZER

(71) Applicants: TOHOKU UNIVERSITY, Sendai-shi, Miyagi (JP); NATIONAL UNIVERSITY CORPORATION HOKKAIDO UNIVERSITY, Sapporo-shi, Hokkaido (JP)

(72) Inventors: Akihide Hibara, Sendai (JP); Manabu Tokeshi, Sapporo (JP); Osamu Wakao, Sapporo (JP)

(73) Assignees: TOHOKU UNIVERSITY, Sendai-Shi, Miyagi (JP); NATIONAL UNIVERSITY CORPORATION HOKKAIDO UNIVERSITY, Sapporo-Shi, Hokkaido (JP)

( * ) Notice: Subject to any disclaimer, the term of this patent is extended or adjusted under 35 U.S.C. 154(b) by 0 days.

(21) Appl. No.: 15/311,311

(22) PCT Filed: May 8, 2015

(86) PCT No.: PCT/JP2015/063282
§ 371 (c)(1),
(2) Date: Nov. 15, 2016

(87) PCT Pub. No.: WO2015/174332
PCT Pub. Date: Nov. 19, 2015

(65) Prior Publication Data
US 2017/0074796 A1    Mar. 16, 2017

(30) Foreign Application Priority Data
May 16, 2014  (JP) .................................. 2014-102446

(51) Int. Cl.
*G01N 21/64* (2006.01)
*G02F 1/13* (2006.01)
*G01N 33/542* (2006.01)

(52) U.S. Cl.
CPC .......... *G01N 21/6445* (2013.01); *G01N 21/64* (2013.01); *G01N 21/6456* (2013.01);
(Continued)

(58) Field of Classification Search
CPC .... G01N 21/6456; G01N 21/64; G01N 21/21; G01N 21/6445
See application file for complete search history.

(56) References Cited

U.S. PATENT DOCUMENTS 5,394,199 A * 2/1995 Flower ................. A61B 3/1241
351/205
2009/0275145 A1 11/2009 Lakowicz et al.

FOREIGN PATENT DOCUMENTS

JP    2005292662 A    10/2005
JP    2009511998 A    3/2009
(Continued)

OTHER PUBLICATIONS

International Preliminary Report on Patentability corresponding to Application No. PCT/JP2015/063282; Date of Mailing: Dec. 22, 2015, with English translation.
(Continued)

*Primary Examiner* — Marcus Taningco
(74) *Attorney, Agent, or Firm* — Cantor Colburn LLP (57) ABSTRACT

An excitation light source emits excitation light to a target sample. An image sensor includes pixels arranged one-dimensionally or two-dimensionally, and receives measurement light from the sample according to the excitation light. A polarization selector arranged between the sample and image sensor includes pixels arranged one-dimensionally or two-dimensionally. Each pixel receives a corresponding portion of the measurement light, selects light having a polarization direction that corresponds to a driving signal applied to the pixels, and supplies this light to the image
(Continued)

sensor. A measurement control unit supplies the cyclic driving signal having a first period $T_1$, and acquires data $I_1$, $I_2$, $I_3$, and $I_4$ from each pixel of the image sensor for each exposure time segment $T_2=T_1/4$ obtained by dividing the first period $T_1$ by 4.

6 Claims, 9 Drawing Sheets

(52) U.S. Cl.
CPC .............. *G01N 33/542* (2013.01); *G02F 1/13* (2013.01); *G01N 2201/0675* (2013.01)

(56) References Cited

FOREIGN PATENT DOCUMENTS

JP            2012132838  A       7/2012
JP            2013195203  A       9/2013

OTHER PUBLICATIONS

International Search Report corresponding to Application No. PCT/JP2015/063282; Date of Mailing: Jul. 21, 2015, with English translation.

Written Opinion of the International Searching Authority corresponding to Application No. PCT/JP2015/063282; Date of Mailing: Jul. 21, 2015, with English translation.

Yaroslaysky et al., "Fluorescence polarization imaging for delineating nonmelanoma skin cancers" Optics Letters, vol. 29, No. 17, Sep. 1, 2004, 3 pages.

* cited by examiner

LIGHT POLARIZATION ANALYZER

CROSS REFERENCE TO RELATED APPLICATIONS

This is the U.S. national stage of application No. PCT/JP2015/063282, filed on May 8, 2015. Priority under 35 U.S.C. §119(a) and 35 U.S.C. §365(b) is claimed from Japanese Application No. 2014-102446, filed May 16, 2014, the disclosure of which is also incorporated herein by reference.

BACKGROUND OF THE INVENTION

1. Field of the Invention

The present invention relates to a light polarization analyzer usable for a fluorescence depolarization method or the like.

2. Description of the Related Art

As a method for measuring the viscosity of a liquid, or as a bioanalysis technique, a fluorescence depolarization method is employed. With the fluorescence depolarization method, a parallel component $I_{II}$ and a perpendicular component $I_\perp$ with respect to the excitation light polarization direction of excitation light are each measured, so as to detect a fluorescence polarization degree P as represented by $P=(I_{II}-I_\perp)/(I_{II}+I_\perp)$. By employing such a fluorescence depolarization method, such an arrangement allows an immune assay method, which ordinarily requires multiple steps, to be performed as a single-step operation.

However, with such a fluorescence depolarization method, the fluorescence polarization degree P is detected by means of calculation after measurement of a pair of light components, i.e., $I_{II}$ and $I_\perp$ having polarization directions that are perpendicular to each other, which is troublesome. Thus, there is almost no known arrangement that provides multi-sampling measurement. In a case of measuring multiple points at the same time, such an arrangement is required to repeatedly perform single-point measurement with respect to the focal point while scanning the focal point. Such an arrangement requires a long measurement time, a large-size apparatus, and high costs, which are problems.

SUMMARY OF THE INVENTION

The present invention has been made in order to solve such a problem. Accordingly, it is an exemplary purpose of an embodiment of the present invention to provide a light polarization analyzer that is capable of measuring multiple points at the same time.

An embodiment of the present invention relates to a light polarization analyzer. The light polarization analyzer comprises: an excitation light source that emits an excitation light to a sample to be measured; an image sensor comprising multiple pixels arranged in a one-dimensional manner or otherwise a two-dimensional manner so as to receive a measurement light generated from the sample in response to the excitation light; a polarization selector that is arranged between the sample and the image sensor, that comprises multiple pixels arranged in a one-dimensional manner or otherwise a two-dimensional manner, and that is configured such that each pixel receives a corresponding portion of the measurement light, selects the measurement light having a polarization direction that corresponds to a driving signal applied to the pixel, and supplies the selected measurement light to the image sensor; and a measurement control unit that supplies the driving signal configured as a cyclic signal having a first period $T_1$ to each pixel of the polarization selector, and that acquires data $I_1$ through $I_N$ from each pixel of the image sensor for exposure time segments $T_{2\_1}$ through $T_{2\_N}$, each of which have an exposure period $T_2=T_1/N$ obtained by dividing the first period $T_1$ by N (N represents a plural integer).

The data $I_1$ through $I_N$ may be obtained by integration, addition, or accumulation of the input light input to the image sensor for the respective exposure time segments $T_{2\_1}$ through $T_{2\_N}$. With such an embodiment, by employing the polarization selector, such an arrangement is capable of measuring two polarization components that are orthogonal to each other. This allows the state of a sample to be acquired in the form of one-dimensional or otherwise two-dimensional multi-point information based on the data $I_1$ through $I_N$ acquired for the respective pixels.

Also, an arrangement may be made in which N=4, and data $I_1$ through $I_4$ are acquired.

In this case, such an arrangement is capable of acquiring the AC amplitude (AC value) of the measurement light.

Also, the measurement control unit may calculate $\sqrt{\{(I_1-I_3)^2+(I_2-I_4)^2\}}/(I_1+I_2+I_3+I_4)$ for every pixel, so as to measure a polarization degree P.

Also, the measurement control unit may acquire intermediate data $Im_1$ through $Im_M$ from each pixel of the image sensor for exposure time segments $T_{3\_1}$ through $T_{3\_M}$, each of which have an exposure period $T_3=T_1/M$ obtained by dividing the first period $T_1$ by a plural number, i.e., M (M≥3, M≠N). Also, the measurement control unit may convert the intermediate data $Im_1$ through $Im_M$ into the data $I_1$ through $I_N$.

Also, the polarization selector may comprise a liquid crystal panel and a polarizer.

Such an arrangement is capable of selecting the measurement light having a polarization direction that corresponds to the driving signal.

Also, the driving signal may have a cyclic waveform such as a sine wave, a rectangular wave, a sawtooth wave, a trapezoidal wave, or the like.

Examples as represented by "the driving signal having a given waveform (e.g., a sinusoidal waveform)" also include the driving signal having a waveform obtained by approximating the given waveform, in addition to a driving signal having a strictly sinusoidal waveform.

It is to be noted that any arbitrary combination or rearrangement of the above-described structural components and so forth is effective as and encompassed by the present embodiments. Moreover, this summary of the invention does not necessarily describe all necessary features so that the invention may also be a sub-combination of these described features.

BRIEF DESCRIPTION OF THE DRAWINGS

The invention will now be described based on preferred embodiments which do not intend to limit the scope of the present invention but exemplify the invention. All of the features and the combinations thereof described in the embodiment are not necessarily essential to the invention.

DETAILED DESCRIPTION OF THE INVENTION

Description will be made below regarding preferred embodiments according to the present invention with reference to the drawings. The same or similar components, members, and processes are denoted by the same reference numerals, and redundant description thereof will be omitted as appropriate.

The embodiments have been described for exemplary purposes only, and are by no means intended to restrict the present invention. Also, it is not necessarily essential for the present invention that all the features or a combination thereof be provided as described in the embodiments.

Figure 1:
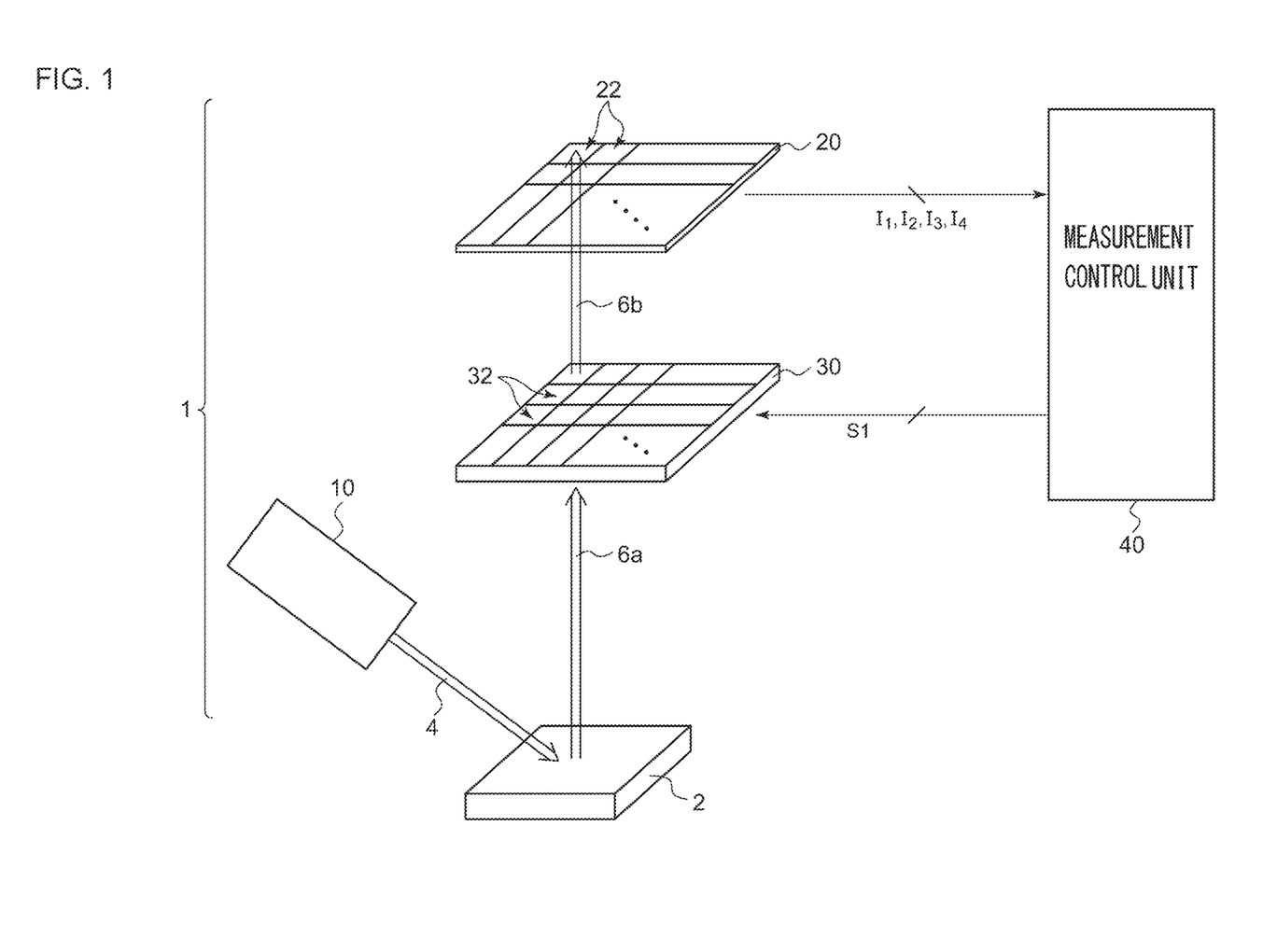
FIG. 1 is a diagram showing a basic configuration of a light polarization analyzer according to an embodiment.

FIG. 1 is a diagram showing a basic configuration of a light polarization analyzer 1 according to an embodiment. The light polarization analyzer 1 mainly includes an excitation light source 10, an image sensor 20, a polarization selector 30, and a measurement control unit 40. For simplicity of description and ease of understanding, description will be made below regarding an arrangement that measures a real image without involving image zooming.

The excitation light source 10 emits an excitation light 4 to a sample 2 to be measured. For example, the excitation light source 10 is configured as a laser device. In the present embodiment, the sample 2 is configured as a fluorescent material. The sample 2 is excited by the excitation light 4, and emits light that corresponds to the excitation light 4 thus received. Accordingly, the wavelength of the excitation light source 10 is selected according to the sample 2. A measurement light 6a (fluorescence) emitted from the sample 2 has a polarization direction that changes according to the states of the sample 2, examples of which include the temperature of the sample 2, the viscosity of the sample 2, the amount of a particular material included in the sample 2, and the kind of such a particular material.

The image sensor 20 includes multiple pixels 22 arranged in a one-dimensional manner or a two-dimensional manner such that they receive the measurement light 6a emitted from the sample 2 in response to the excitation light 4. Examples of the image sensor 20 that can be employed include a CCD (Charge Coupled Device), a CMOS sensor, a photodiode array, and the like. The kind of such an image sensor 20 is not restricted in particular. As described later, the image sensor 20 is required to be configured to control and set the exposure time.

The polarization selector 30 includes multiple pixels 32 arranged in a one-dimensional manner or a two-dimensional manner. The polarization selector 30 is arranged between the sample 2 and the image sensor 20. In the present embodiment, the polarization selector 30 is configured as a transmissive device. Each pixel 32 is configured to receive a corresponding part of the measurement light 6a via its back face, to select a measurement light 6b having a polarization direction that corresponds to a driving signal S1 applied to the pixel 32, and to supply the measurement light 6b thus selected to the image sensor 20.

For example, when the driving signal S1 is set to a given value $S_{MIN}$, each pixel 32 selects the polarization component $I_\perp$ having a predetermined first polarization direction. When the driving signal S1 is set to a different value $S_{MAX}$, each pixel 32 selects the polarization component $I_{II}$ having a second polarization direction that is orthogonal to the first polarization direction. Each pixel 32 allows the polarization component thus selected to pass through.

The measurement control unit 40 supplies the driving signal S1 configured as a cyclic signal having a first period $T_1$ to each pixel 32 of the polarization selector 30. Furthermore, the measurement control unit 40 acquires data $I_1$ through $I_N$ from the respective pixels of the image sensor 20 in synchronization with the driving signal S1 with the exposure time segments $T_{2\_1}$ through $T_{2\_N}$ each having a time period $T_2=T_1/N$ obtained by dividing the first period $T_1$ by N (N represents an integer). Description will be made in the present embodiment regarding an arrangement in which N=4.

The above is the basic configuration of the light polarization analyzer 1. Next, description will be made regarding the polarization selector 30.

Figure 2A:
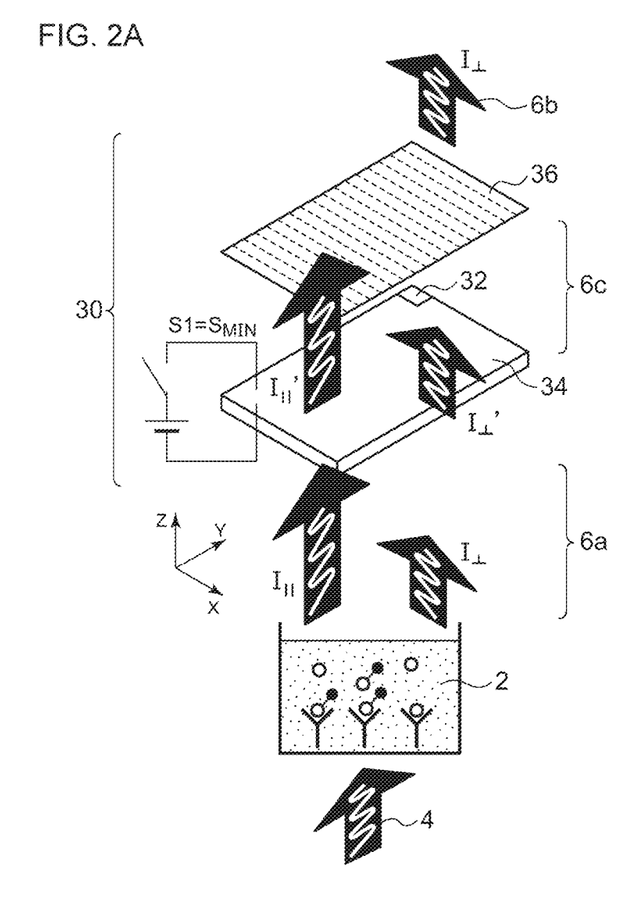
FIGS. 2A and 2B are diagrams each showing an example configuration and an operation mechanism of a polarization selector.
Figure 2B:
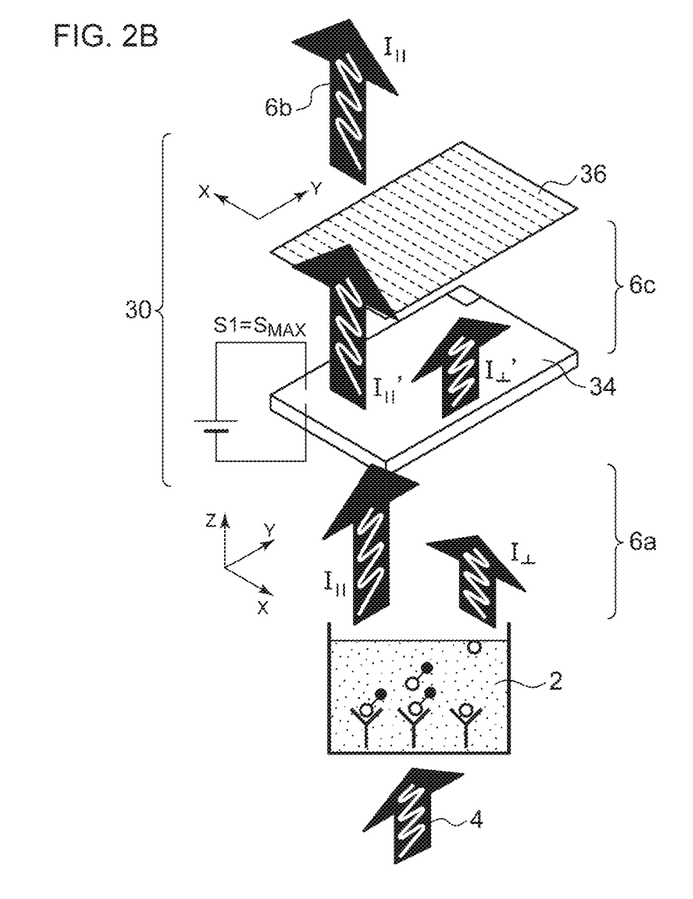

FIGS. 2A and 2B are diagrams each showing an example configuration and an operation mechanism of the polarization selector 30.

For example, the polarization selector 30 is configured as a transmissive element, which can be configured as a combination of a liquid crystal panel 34 and a polarizer 36. The liquid crystal panel 34 includes multiple pixels 35 and unshown drivers and the like such as a gate driver and a source driver. Each pixel 35 is configured such that the driving signal S1 can be applied to the pixels 35 independently. Each pixel 35 is configured as a polarizing element that rotates the polarization direction of the light input from the back face thereof by an angle $\theta$ that corresponds to the level (magnitude) of the driving signal S1. For example, when the driving signal S1 is set to $S_{MIN}$, the rotational angle $\theta$ is set to 0 degrees. When the driving signal S1 is set to $S_{MAX}$, the rotational angle $\theta$ is set to 90 degrees. When the driving signal S1 is set to an intermediate value, the rotational angle $\theta$ is set to a corresponding intermediate value. The relation between the driving signal S1 and the rotational angle $\theta$ is configured to have a relation to a so-called $\gamma$-curve. Each pixel 35 corresponds to the pixel 32 shown in FIG. 1. For example, in a case in which the liquid crystal panel 34 is configured as an 8-bit liquid crystal panel, the driving signal S1 is configured as a 256 (=$2^8$) multi-level signal. In this case, $S_{MIN}$=0 and $S_{MAX}$=255 hold true.

The polarizer 36 is arranged such that it overlays the liquid crystal panel 34. Such an arrangement allows the polarization component having a predetermined polarization direction (X direction in FIG. 2) to selectively pass through. On the other hand, such an arrangement blocks (absorbs or reflects) the polarization component having a polarization direction (Y direction in FIG. 2) that is orthogonal to the X direction.

Typically, commercially available LCD panels (Liquid Crystal Panels) each include the liquid crystal panel 34 and a pair of polarizers arranged such that the liquid crystal panel 34 is interposed between them and such that the pair of polarizers have polarization directions that are orthogonal to each other. The polarization selector 30 according to the embodiment has a configuration that can be obtained by disaggregating such a commercially available LCD panel such that one of the pair of polarizers is removed.

As shown in FIG. 2A, the measurement light 6a includes the polarization component $I_{II}$ having the X polarization direction and the polarization component $I_{\perp}$ having the Y polarization direction. FIG. 2A shows a case in which $S1=S_{MIN}$. In this case, each pixel 35 of the liquid crystal panel 34 does not rotate the polarization directions of the polarization component $I_{II}$ having the X polarization direction and the polarization component $I_{\perp}$, i.e., passes the polarization components without rotating the polarization directions. After the measurement light 6a passes through the liquid crystal panel 34, the polarization component $I_{II}'$ having the Y polarization direction, which is one from among the polarization components of the measurement light 6c, cannot pass through the polarizer 36. On the other hand, the polarization component $I_{\perp}'$ having the X polarization direction can pass through the polarizer 36. That is to say, in a state shown in FIG. 2A, from among the polarization components of the measurement light 6a, the polarization component $I_{\perp}$ having the X polarization direction is selected.

In a state shown in FIG. 2B, the driving signal S1 is set to $S1=S_{MAX}$. In this case, each pixel 35 of the liquid crystal panel 34 allows the polarization directions of the polarization component $I_{II}'$ having the X polarization direction and the polarization component $I_{\perp}$ to pass through after the polarization directions are rotated by 90 degrees. With such an arrangement, after the measurement light 6c passes through the liquid crystal panel 34, the polarization component $I_{\perp}'$ having the Y polarization direction, which is one of the polarization components of the measurement light 6c, cannot pass through the polarizer 36. On the other hand, the polarization component $I_{II}'$ having the X polarization direction can pass through the polarizer 36. That is to say, in a state shown in FIG. 2B, the polarization component $I_{II}$ having the Y polarization direction is selected from among the components of the measurement light 6a.

Directing attention to the polarization component $I_{\perp}$ of the measurement light 6a having the X polarization direction, when $S1=S_{MIN}$ as shown in FIG. 2A, the transmittance $\alpha_{\perp}$ for the polarization component $I_{\perp}$ is set to the maximum transmittance (almost 1). When $S1=S_{MAX}$ as shown in FIG. 2B, the transmittance $\alpha_{\perp}$ is set to the minimum transmittance (almost 0). When the driving signal S1 is set to an intermediate state ($S_{MAX}<S1<S_{max}$), the transmittance $\alpha_{\perp}$ is set to an intermediate value that corresponds to the driving signal S1. Similarly, directing attention to the polarization component $I_{II}$ of the measurement light 6a having the Y polarization direction, when $S1=S_{MIN}$ as shown in FIG. 2A, the transmittance $\alpha_{II}$ for the polarization component $I_{II}$ is set to the minimum transmittance (almost 0). When $S1=S_{MAX}$ as shown in FIG. 2B, the transmittance $\alpha_{II}$ is set to the maximum transmittance (almost 1). When the driving signal S1 is set to an intermediate state ($S_{MAX}<S1<S_{MAX}$), the transmittance $\alpha_{II}$ is set to an intermediate value that corresponds to the driving signal S1.

The mechanism of the polarization selector 30 can be understood as follows. That is to say, after the polarization direction of the measurement light 6a is rotated by a rotational angle θ by means of the liquid crystal panel 34 according to the driving signal S1 that can be set as desired, the polarization selector 30 allows the light component having a polarization direction that matches the X direction to pass through.

The above is an example configuration of the polarization selector 30. Next, description will be made regarding the operation of the light polarization analyzer 1 shown in FIG. 1.

Figure 3A:
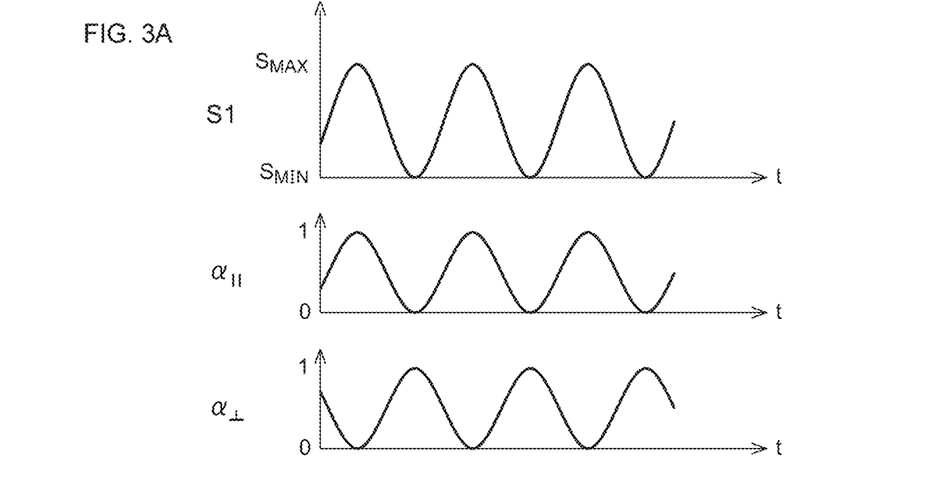
FIGS. 3A through 3C are operation waveform diagrams each showing the operation of the light polarization analyzer.
Figure 3B:
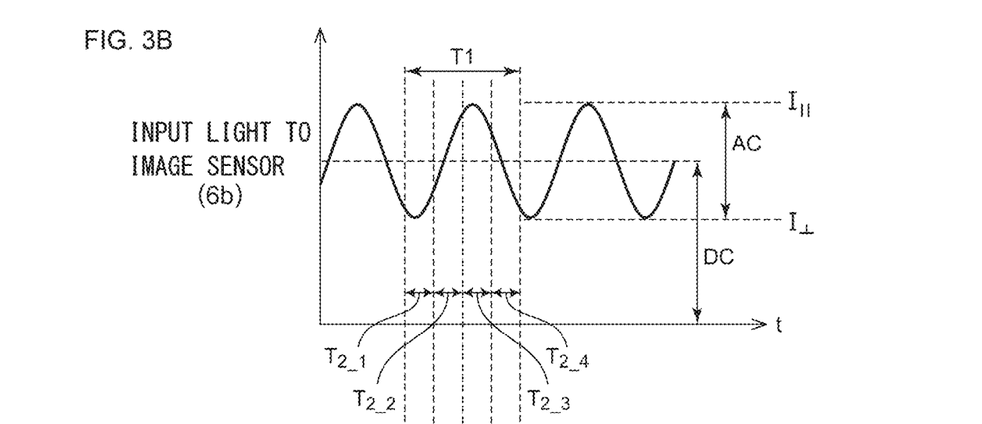
Figure 3C:
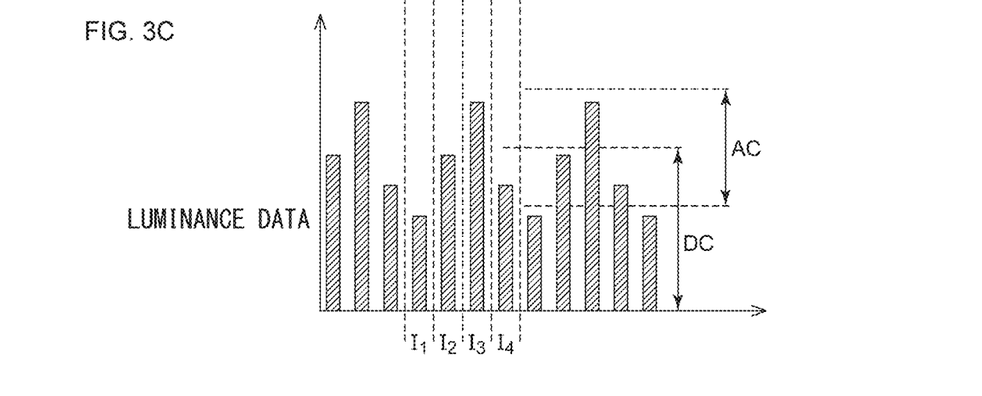

FIGS. 3A through 3C are operation waveform diagrams each showing an operation of the light polarization analyzer 1. FIGS. 3A through 3C each show an operation of a given pixel of the polarization selector 30 and an operation of a corresponding pixel of the image sensor 20.

As shown in FIG. 3A, the driving signal S1 is configured to be a sine wave having a period $T_1$. As a result, the polarization selector 30 allows the polarization component $I_{II}$ to pass through with the transmittance $\alpha_{II}$ that changes in phase with the driving signal S1. On the other hand, the polarization selector 30 allows the polarization component $I_{\perp}$ to pass through with the transmittance $\alpha_{\perp}$ that changes in reverse phase with the driving signal S1.

FIG. 3B shows a case in which the measurement light 6a emitted from the sample 2 is configured as a luminance having a steady relation of $I_{II}>I_{\perp}$. When the driving signal S1 is set to the maximum value $S_{MAX}$, the input light 6b input to the image sensor 20 corresponds to the polarization component $I_{II}$. When the driving signal S1 is set to the maximum value $S_{MIN}$, the input light 6b input to the image sensor 20 matches the polarization component $I_{\perp}$.

As shown in FIG. 3C, the image sensor 20 operates in synchronization with the polarization selector 30, i.e., in synchronization with the driving signal S1. The measurement control unit 40 divides the first period $T_1$ of the driving signal S1 into four periods each having a second period $T_2$, which are used as the exposure time segments $T_{2\_1}$ through $T_{2\_4}$ to be set for the image sensor 20. The image sensor 20 outputs luminance data $I_1$, $I_2$, $I_3$, and $I_4$ respectively indicating the amounts of received light (luminance levels) of the input light 6b respectively acquired in the exposure time segments $T_{2\_1}$ through $T_{2\_4}$.

The above is the operation of the light polarization analyzer 1. The luminance data $I_1$ through $I_4$ can be used for the calculation of the fluorescence polarization degree P.

In a case in which the phase relation between each pixel of the image sensor 20 and the corresponding pixel of the polarization selector 30 can be controlled with high precision, the polarization component $I_{\perp}$ can be acquired as the luminance data $I_1$ obtained in the exposure time segment $T_{2\_1}$ that corresponds to the minimum value $S_{MIN}$ of the driving signal S1. Furthermore, the polarization component $I_{II}$ can be acquired as the luminance data $I_3$ obtained in the exposure time segment $T_{2\_3}$ that corresponds to the maximum value $S_{MAX}$ of the driving signal S1. In this case, the fluorescence polarization degree P can be calculated based on the following Expression (1).

$$P=(I_{II}-I_{\perp})/(I_{II}+I_{\perp})=(I_3-I_1)/(I_3+I_1) \quad (1)$$

However, it is difficult for all the pixels of the image sensor 20 and the polarization selector 30 to maintain such a uniform phase relation between the phase of the driving signal S1 and the exposure time segments $T_{2\_1}$ through $T_{2\_4}$. That is to say, at a given pixel, the exposure time segment $T_{2\_1}$ corresponds to the minimum value $S_{MIN}$ of the driving signal S1. However, in some cases, at a different pixel, the minimum value $S_{MIN}$ corresponds to a different exposure time segment $T_{2\_2}$, $T_{2\_3}$, or $T_{2\_4}$. In this case, the fluorescence polarization degree P cannot be calculated based on Expression (1).

In order to solve such a problem, the measurement control unit 40 may perform the following signal processing.

As shown in FIG. 3B, $(I_{II}-I_\perp)$ corresponds to the AC amplitude (which will also be referred to as the "AC value") of the measurement light 6b. Furthermore, $(I_{II}+I_\perp)/2$ corresponds to the DC component (which will also be referred to as the "DC value") of the measurement light 6b.

$$(I_{II}-I_\perp)=AC$$

$$(I_{II}+I_\perp)=DC\times 2$$

Accordingly, by acquiring the AC value and the DC value of the measurement light 6b, such an arrangement is capable of calculating the fluorescence polarization degree P based on the following Expression (2).

$$P=(I_{II}-I_\perp)/(I_{II}-I_\perp)=AC/(DC\times 2) \quad (2)$$

The following correspondence relations are hold true between the four luminance data $I_1$ through $I_4$, the AC value, and the DC value.

The DC value is calculated as an average of the luminance data $I_1$ through $I_4$. Accordingly, the DC value is calculated based on the following Expression (3).

$$DC=(I_1+I_2+I_3+I_4)/4 \quad (3)$$

On the other hand, the AC value is calculated based on the following Expression (4).

$$AC=\sqrt{\{(I_1-I_3)^2+(I_2-I_4)^2\}} \quad (4)$$

The value thus calculated corresponds to the RMS (Root Mean Square) of the amplitude calculated based on $I_1$ and $I_3$ and the amplitude calculated based on $I_2$ and $I_4$.

The DC value calculated based on Expression (3) does not depend on the phase relation between the four exposure time segments $T_{2\_1}$ through $T_{2\_4}$ and the driving signal S1, which can be understood by those skilled in this art. Furthermore, in a case in which the driving signal S1 is a sine wave, the AC value calculated based on Expression (4) does not depend on the phase relation between the four exposure time segments $T_{2\_1}$ through $T_{2\_4}$ and the driving signal S1, detailed description of which will be omitted.

Thus, the measurement control unit 40 calculates the following Expression (5), thereby allowing the fluorescence polarization degree P to be measured.

$$P = (I_{II} - I_\perp)/(I_{II} + I_\perp) = AC/(DC \times 2) = \quad (5)$$
$$\sqrt{\{(I_1-I_3)^2+(I_2-I_4)^2\}}/\{(I_1+I_2+I_3+I_4)/4\times 2\} =$$
$$2\times\sqrt{\{(I_1-I_3)^2+(I_2-I_4)^2\}}/(I_1+I_2+I_3+I_4)$$

Furthermore, the polarization component $I_{II}$ having the Y polarization direction, which is one component of the measurement light 6a, can be calculated based on the following Expression (6) using the luminance data $I_1$ through $I_4$.

$$I_{II} = (AC+DC\times 2)/2 = \quad (6)$$
$$[\sqrt{\{(I_1-I_3)^2+(I_2-I_4)^2\}}+\{(I_1+I_2+I_3+I_4)/2\}]/2$$

On the other hand, the polarization component $I_\perp$ having the X polarization direction, which is one component of the measurement light 6a, can be calculated based on the following Expression (7) using the luminance data $I_1$ through $I_4$.

$$I_\perp = (DC\times 2 - AC)/2 = \quad (7)$$
$$[\{(I_1+I_2+I_3+I_4)/2\}-\sqrt{\{(I_1-I_3)^2+(I_2-I_4)^2\}}]/2$$

As described above, the light polarization analyzer 1 according to the embodiment is capable of measuring the fluorescence polarization degree P at the same time for all the pixels arranged in a one-dimensional manner or in a two-dimensional manner without the need to separately measure the polarization component $I_\perp$ having the X polarization direction and the polarization component $I_{II}$ having the Y polarization direction of the measurement light 6a. Furthermore, the light polarization analyzer 1 is capable of measuring the polarization component $I_\perp$ having the X polarization direction and the polarization component $I_{II}$ having the Y polarization direction of the measurement light 6a for all the pixels at the same time.

That is to say, the light polarization analyzer 1 is capable of measuring, at the same time, a one-dimensional distribution or a two-dimensional distribution of the fluorescence polarization degree P for the sample 2, or any one of the distribution of the polarization component $I_\perp$ or the distribution of the component $I_{II}$ for the sample 2, or otherwise a desired combination thereof.

Next, description will be made regarding a specific usage of the light polarization analyzer 1.

Figure 4:
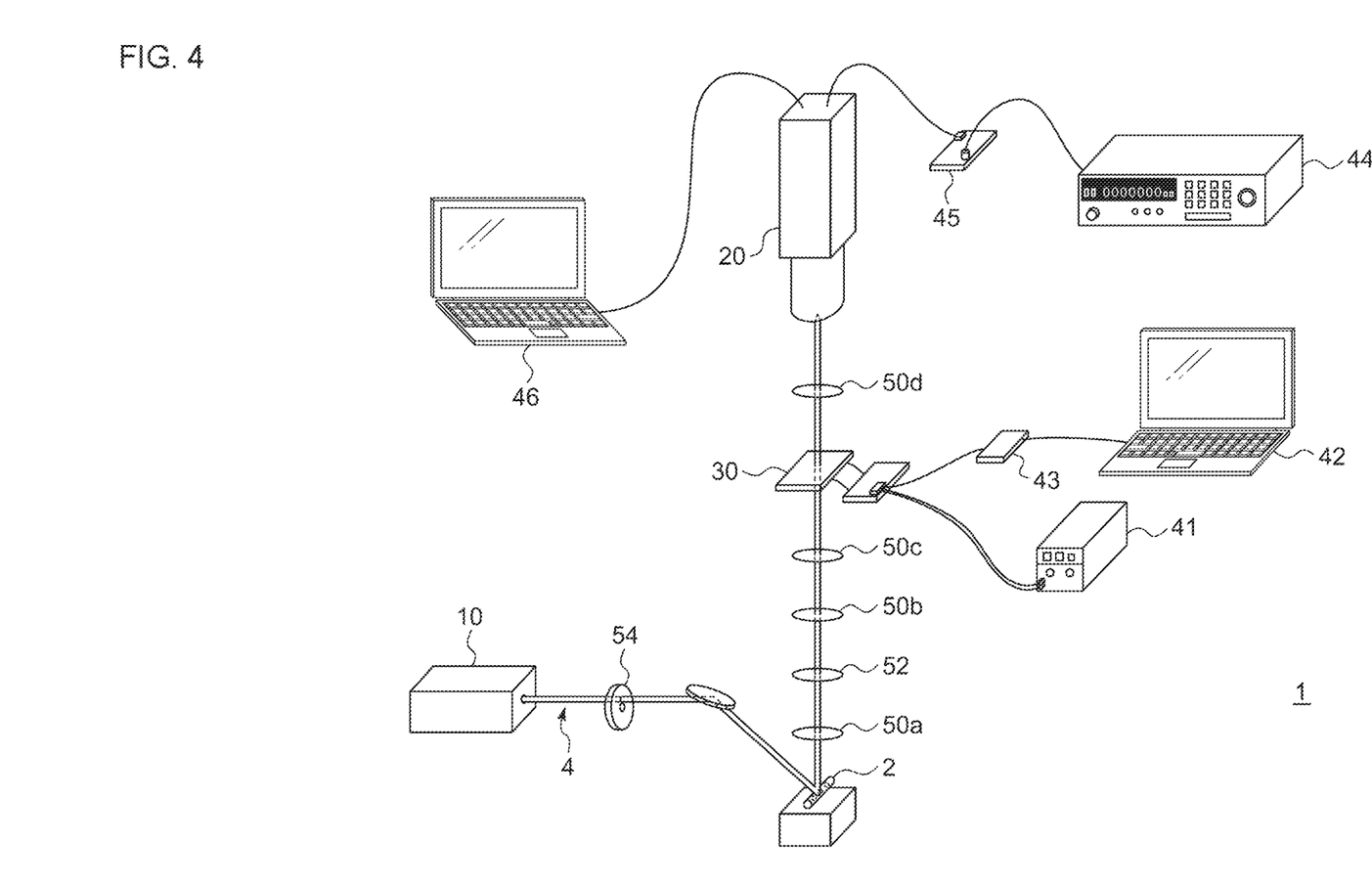
FIG. 4 is a specific example configuration of the light polarization analyzer.

FIG. 4 is a diagram showing a specific example configuration of the light polarization analyzer 1.

The light polarization analyzer 1 shown in FIG. 4 measures the viscosity of a liquid. The light polarization analyzer 1 includes an optical system 50 and a color filter 52 in addition to the excitation light source 10, the image sensor 20, the polarization selector 30, and the measurement control unit 40 shown in FIG. 1.

The sample 2 may be a liquid containing a fluorescent dye as an additive material. For example, the sample 2 is housed within a capillary tube such as a glass tube having a microchannel structure. Examples of such a fluorescent dye include fluorescein and the like.

The excitation light source 10 is configured as a light source that is capable of exciting the luminance dye dissolved in the sample 2. In a case in which fluorescein is employed as such a fluorescent dye, the excitation light source 10 may be configured as a semiconductor laser device that emits laser light having a wavelength of 488 nm. An ND (Neutral Density) filter 54 may be arranged between the excitation light source 10 and the sample 2 in order to adjust the intensity of the excitation light. The image sensor 20 is configured as a CCD array. The polarization selector 30 has a structure shown in FIG. 2. The color filter 52 prevents the excitation light 4 from being input to the image sensor 20.

The optical system 50 enlarges or reduces an image of the sample 2 such that the size of the image matches the sizes of the polarization selector 30 and the image sensor 20. Accordingly, in a case in which the sample 2 has a small size as compared with those of the polarization selector 30 and the image sensor 20, a magnifying optical system is employed. Conversely, in a case in which the sample 2 has a large size as compared with those of the polarization selector 30 and the image sensor 20, a reducing optical system is employed. The optical system 50 can be designed as appropriate based on the sizes of the sample 2, the image sensor 20, and the polarization selector 30, and the position relation between such components, which can be clearly understood by those skilled in this art. That is to say, in the present invention, the optical system 50 is not restricted in particular. In the example shown in FIG. 4, the optical system 50 includes an object lens 50a, an eyepiece lens 50d, and other kinds of lens groups 50b and 50c.

The measurement control unit 40 includes a power supply 41, a computer 42, a converter 43, a function generator 44, a converter 45, and a computer 46.

The power supply 41 supplies a power supply voltage to the polarization selector 30. The computer 42 generates the driving signal S1 to be supplied to each pixel of the polarization selector 30. The converter 43 is configured as an interface that receives an output signal of the computer 42, and that controls each pixel of the polarization selector 30.

The function generator 44 generates a control signal so as to control the exposure time set for the image sensor 20. The converter 45 is configured as an interface that controls the exposure time set for each pixel of the image sensor 20 according to the control signal generated by the function generator 44. The computer 46 receives the image data output from the image sensor 20 in the second period $T_2$, i.e., the luminance data $I_1$ through $I_4$ for each pixel. The computer 46 calculates necessary information based on the luminance data $I_1$ through $I_4$.

It should be noted that the configuration of the measurement control unit 40 is shown for exemplary purposes only. Also, the same functions can be provided using other kinds of devices, which can be clearly understood by those skilled in this art. For example, the computer 42 or 46 may be configured as a combination of a hardware component and a software component each configured as a dedicated component, rather than as a general-purpose computer. Also, the function generator 44 may be configured as a function IC (Integrated Circuit) designed as a dedicated IC, or otherwise as a microcomputer to be controlled in a software manner.

Figure 5A:
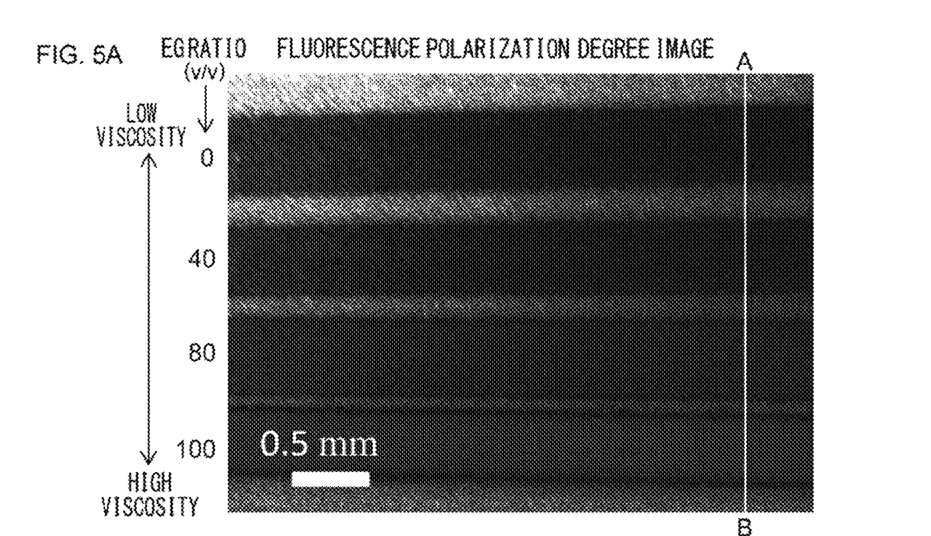
FIGS. 5A through 5C are diagrams each showing the result for the fluorescence polarization degree P that corresponds to a solvent viscosity, which is measured by means of the light polarization analyzer shown in FIG. 4.
Figure 5B:
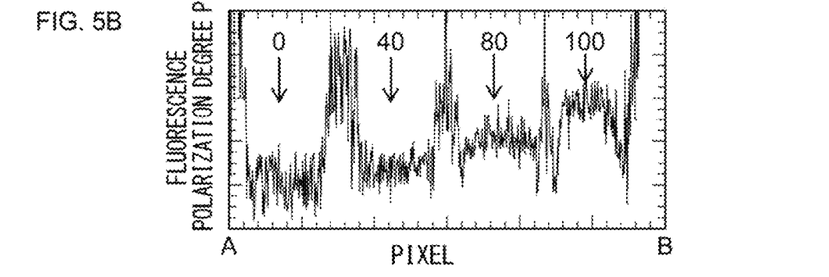
Figure 5C:
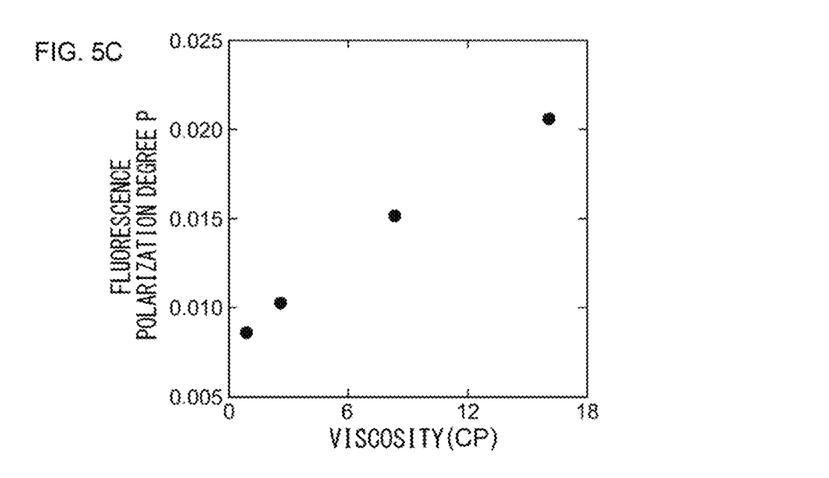

FIGS. 5A through 5C are diagrams each showing a measurement result obtained by means of the light polarization analyzer 1 by measuring the fluorescence polarization degree P that corresponds to the viscosity of the solvent. FIG. 5A shows the fluorescence polarization degree P in the form of an image. FIG. 5B shows the values of the fluorescence polarization degree P. FIG. 5C is a diagram showing the relation between the fluorescence polarization degree and the viscosity (CP).

In this measurement, the driving signal S1 has a frequency of 3 Hz. Accordingly, the first period $T_1$ of the driving signal S1 is 333 ms. The driving signal S1 is configured as a signal that approximates a sine wave. Specifically, the driving signal S1 is configured to have eight divided sections for every period such that the driving signal S1 is maintained at a constant level for each section.

The function generator 44 sets the image sensor 20 such that the image data was output with a frame rate of 12 Hz. In this case, the second period $T_2$ was set to 83.2 ms.

As the sample 2, four glass capillaries (having an outer diameter of 0.5 mm and an inner diameter of 0.32 mm) were prepared. The glass capillaries were arranged such that they respectively housed solutions of water and ethylene glycol (EG) with different respective mixture ratios. The EG ratios thus used were 0, 40, 80, and 100. As the EG ration becomes higher, the viscosity of the solution becomes higher.

As can be clearly understood from FIGS. 5A through 5C, the light polarization analyzer 1 according to the embodiment is capable of measuring the two-dimensional distribution of the fluorescence polarization degree P.

Figure 6A:
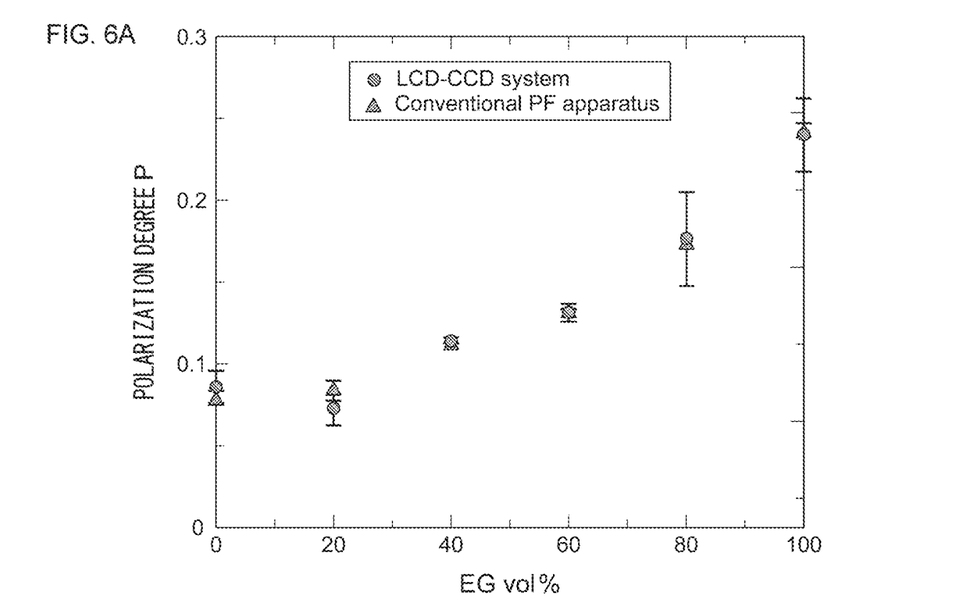
FIGS. 6A and 6B are diagrams respectively showing the relations between the EG ratio and the fluorescence polarization degree P measured by the light polarization analyzer according to the embodiment (LCD-CCD system), and measured using a conventional technique (conventional PF apparatus)

FIG. 6A is a diagram showing the relation between the EG ratio and the fluorescence polarization degree P measured by means of the light polarization analyzer 1 according to the embodiment (LCD-CCD system), and the relation between them measured by means of a conventional technique (conventional PF apparatus). As shown in FIG. 6A, the light polarization analyzer 1 is capable of measuring the fluorescence polarization degree P with the same precision as that provided by such a conventional technique. It should be noted that such a conventional technique does not support two-dimensional image acquisition.

Figure 6B:
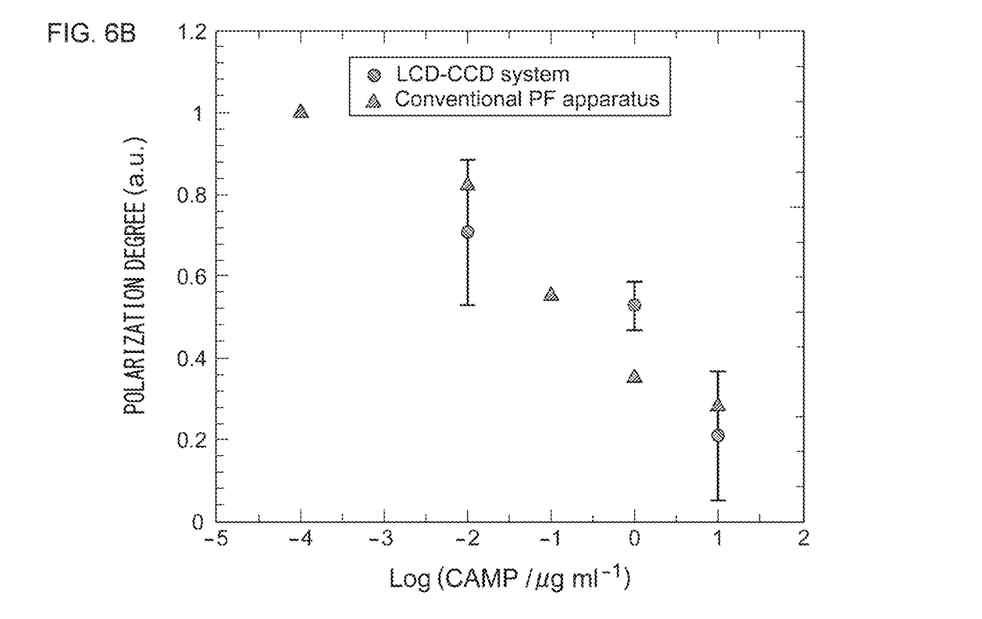

FIG. 6B shows a result obtained by means of the light polarization analyzer 1 by measuring a concentration of chloramphenicol (a bacterially-derived antibiotic) using an immune assay method. The horizontal axis represents the chloramphenicol concentration in a logarithmic manner. The vertical axis represents the normalized polarization degree P. In addition, FIG. 6B shows the polarization degree P measured using a conventional method. As described above, the light polarization analyzer 1 can be employed to measure a concentration of an antibiotic using an immune assay method.

Description has been made above regarding the present invention with reference to the embodiment. The above-described embodiment has been described for exemplary purposes only, and is by no means intended to be interpreted restrictively. Rather, it can be readily conceived by those skilled in this art that various modifications may be made by making various combinations of the aforementioned components or processes, which are also encompassed in the technical scope of the present invention. Description will be made below regarding such modifications.

[First Modification]

Description has been made in the embodiment regarding an arrangement in which the driving signal S1 is a sine wave. However, the present invention is not restricted to such an arrangement. Also, the driving signal may be configured as a cyclic signal such as a rectangular wave or a trapezoidal wave instead of a sine wave. Also, the driving signal S1 may have a waveform obtained by approximating any one of the aforementioned waveforms. Also, the driving signal S1 may be configured as a multi-level signal obtained by quantizing (discretizing) any one of the aforementioned waveforms.

[Second Modification]

Figure 7:
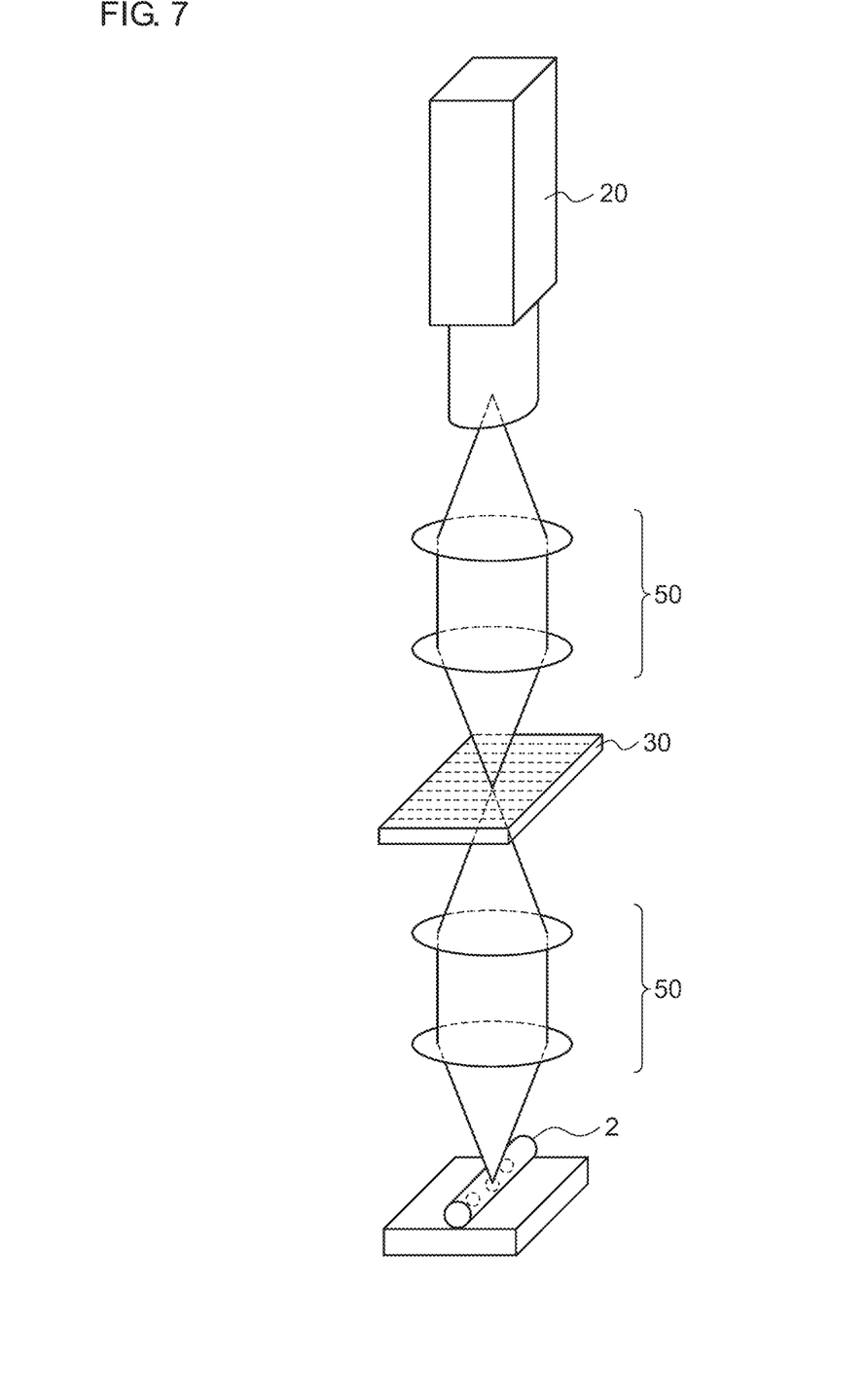
FIG. 7 is a diagram showing a modification of an optical system of the light polarization analyzer.

FIG. 7 is a diagram showing a modification of the optical system of the light polarization analyzer 1. The polarization selector 30 can be arranged at a desired position between the sample 2 and the image sensor 20. In a case in which polarization analysis is to be performed for a selected position, the polarization selector 30 is preferably arranged on an imaging plane as shown in FIG. 7. In a case in which it can be assumed that the polarization selector 30 has a sufficiently small thickness, the polarization selector 30 may be arranged in the vicinity of the sample 2 or otherwise the image sensor 20.

[Third Modification]

Description has been made in the embodiment regarding an arrangement in which the polarization selector 30 is configured using the liquid crystal panel 34. However, the present invention is not restricted to such an arrangement. Also, the polarization selector 30 may be configured using a known or prospectively available device having the same function as that of a combination of the liquid crystal panel 34 and the polarizer 36, instead of such a combination. Also, the polarization selector 30 is not restricted to such a transmissive device. Also, the polarization selector 30 may be configured as a reflective device.

[Fourth Modification]

Description has been made in the embodiment regarding an arrangement in which fluorescence is measured as the measurement light. However, the present invention is not restricted to such an arrangement. For example, phosphorescence may be measured instead of fluorescence. In a case in which second-harmonic light or third-harmonic light is emitted from the sample due to a non-linear optical phenomenon, such light may be measured. That is to say, the light polarization analyzer 1 may use, as the measurement target, various kinds of light having a polarization state that corresponds to the state of the sample 2.

[Fifth Modification]

The usage of the light polarization analyzer 1 is not restricted in particular. In addition to supporting the immune assay, the light polarization analyzer 1 may be used for the following interaction measurements.

Interaction between carbohydrates and proteins.
Interaction between proteins.
Interaction between DNA and proteins.
Interaction between peptides and proteins.
Interaction between ligands and receptors.

[Sixth Modification]

Description has been made in the embodiment regarding an arrangement in which N=4. Such an arrangement acquires the luminance data $I_1$ through $I_4$ respectively indicating the values obtained by integrating the input light received by the image sensor for the four exposure time segments $T_{2\_1}$ through $T_{2\_N}$. The fluorescence polarization degree P is calculated based on the luminance data $I_1$ through $I_4$. However, the present invention is not restricted to such an arrangement. Also, an arrangement may be made in which N≠4. Such an arrangement also acquires the state of the sample in the form of one-dimensional or otherwise two-dimensional multi-point information based on the luminance data $I_1$ through $I_N$. For example, as can be clearly understood, in a case in which information other than the AC value, DC value, or otherwise the luminance polarization degree P is required, an arrangement may preferably be made in which N≠4. As described later (regarding the DC value and AC value), in a case of employing the driving signal S1 that is a sine wave or otherwise particular other kinds of waveforms, such an arrangement is preferably made in which N=4 in order to acquire the AC value and DC value, and accordingly the fluorescence polarization degree P. However, in a case in which the driving signal is configured as other kinds of waveforms, in some cases, such an arrangement is preferably made in which N≠4 in order to acquire the AC value and DC value, and accordingly the fluorescence polarization degree P.

[Seventh Modification]

Description has been made in the embodiment regarding an arrangement that directly acquires, by measurement, the N luminance data $I_1$ through $I_N$, which are required to calculate the value to be generated in the final stage such as the AC value, DC value, or the fluorescence polarization degree P. However, the present invention is not restricted to such an arrangement. For example, an arrangement may be made configured to acquire intermediate data $Im_1$ through $Im_M$ from each pixel of the image sensor with multiple, i.e., M (M≥3, M≠N) exposure time segments $T_{3\_1}$ through $T_{3\_M}$ having an exposure period $T_3=T_1/M$ obtained by dividing the first period $T_1$. The intermediate data $Im_1$ through $Im_M$ thus acquired may be converted into the N luminance data $I_1$ through $I_N$ required to calculate the value to be generated in the final stage.

For example, in a case in which M=8, the luminance data $I_1$ may be calculated based on the intermediate data $Im_1$ and $Im_2$. Also, the luminance data $I_2$ may be calculated based on the intermediate data $Im_3$ and $Im_4$. Also, the luminance data $I_3$ may be calculated based on the intermediate data $Im_5$ and $Im_6$. Also, the luminance data $I_4$ may be calculated based on the intermediate data $Im_7$ and $Im_8$.

As another example, an arrangement may be made in which M=3, 5, 6, or 7, in order to acquire the luminance data $I_1$ through $I_4$ required to calculate the AC value, the DC value, the fluorescence polarization degree P, or the like.

$$M=3 \quad \quad (i)$$

Examples of conversion Expressions are provided below.

$$I_1 = \tfrac{3}{4} \times Im_1$$

$$I_2 = \tfrac{1}{4} \times Im_1 + \tfrac{1}{2} \times Im_2$$

$$I_3 = \tfrac{1}{2} \times Im_2 + \tfrac{1}{4} \times Im_3$$

$$I_4 = \tfrac{3}{4} \times Im_3$$

Figure 8A:
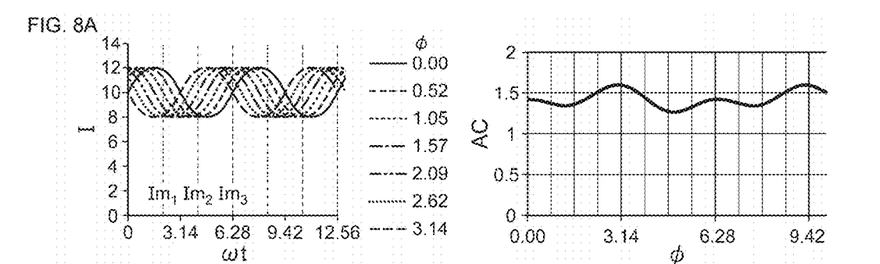
FIGS. 8A through 8D are waveform diagrams respectively showing the operations in a case in which M=3, 5, 6, and 7.

FIG. 8A is a waveform diagram showing an arrangement in which M=3. The left-hand graph shows the relation between the sine wave I and the exposure time segments $T_{3\_1}$ through $I_{3\_3}$. The right-hand graph shows the calculation result for the phase $\phi$ and the AC value.

$$I(\omega t) = DC + AC \times \sin(\Omega t + \phi)$$

$$T_{3\_1} = 0 \text{ to } 2\pi/3$$

$$T_{3\_2} = 2\pi/3 \text{ to } 4\pi/3$$

$$T_{3\_3} = 4\pi/3 \text{ to } 2\pi$$

The calculation result for the AC value becomes a value that corresponds to the exposure time segments $T_{3\_1}$ through $I_{3\_3}$ and the phase difference T of the sine wave signal. The AC value is ideally 2. However, the AC value calculated based on the aforementioned conversion expression using the luminance data $I_1$ through $I_4$ is 1.42±0.10. This means that such an arrangement leads to a reduction in sensitivity to 70% with a relative error of 7%. In a case in which such a reduction in sensitivity is allowable, by calculating the AC value multiple times with random phase differences $\phi$, such an arrangement provides the AC value with sufficiently small error.

$$M=5 \quad \quad (ii)$$

Examples of conversion Expressions are provided below.

$$I_1 = Im_1 + \tfrac{1}{4} \times Im_2$$

$$I_2 = \tfrac{3}{4} \times Im_2 + \tfrac{1}{2} \times Im_3$$

$$I_3 = \tfrac{1}{2} \times Im_3 + \tfrac{3}{4} \times Im_4$$

$$I_4 = \tfrac{3}{4} \times Im_4 + Im_5$$

Figure 8B:
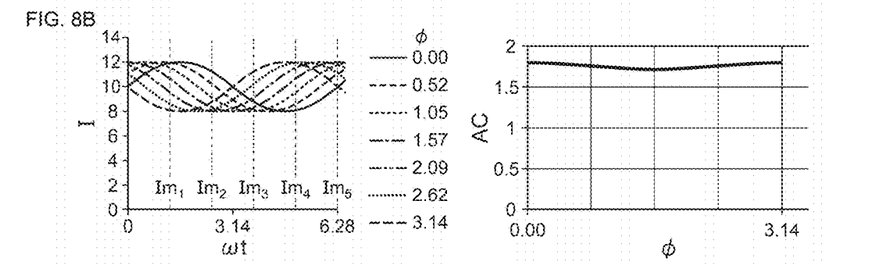

FIG. 8B is a waveform diagram showing a case in which M=5. The calculation value of the AC value, the ideal value of which is 2, becomes 1.76±0.03. This means that such an arrangement leads to a reduction in sensitivity to 85% with a relative error of 1%. In a case in which such a reduction in sensitivity is allowable, by calculating the AC value multiple times with random phase differences $\phi$, such an arrangement provides the AC value with sufficiently small error.

$$M=6 \quad \text{(iii)}$$

Examples of conversion Expressions are provided below.

$$I_1=Im_1+\tfrac{1}{2}\times Im_2$$

$$I_2=\tfrac{1}{2}\times Im_2+Im_3$$

$$I_3=Im_4+\tfrac{1}{2}\times Im_5$$

$$I_4=\tfrac{1}{2}\times Im_5+Im_6$$

Figure 8C:
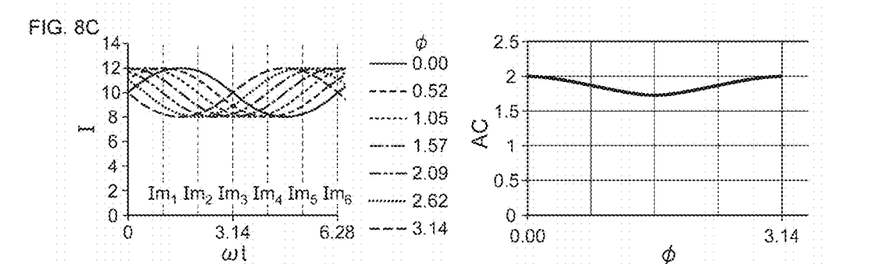

FIG. 8C is a waveform diagram showing a case in which M=6. The calculation value of the AC value, the ideal value of which is 2, becomes 1.89±0.10. This means that such an arrangement leads to a reduction in sensitivity to 94% with a relative error of 5%. In a case in which such a reduction in sensitivity is allowable, by calculating the AC value multiple times with random phase differences $\phi$, such an arrangement provides the AC value with sufficiently small error.

$$M=7 \quad \text{(iv)}$$

Example conversion Expressions are provided below.

$$I_1=Im_1+\tfrac{3}{4}Im_2$$

$$I_2=\tfrac{1}{4}\times Im_2+Im_3+\tfrac{1}{2}\times Im_4$$

$$I_3=\tfrac{1}{2}\times Im_4+Im_5+\tfrac{1}{4}\times Im_6$$

$$I_4=\tfrac{3}{4}\times Im_6+Im_7$$

Figure 8D:
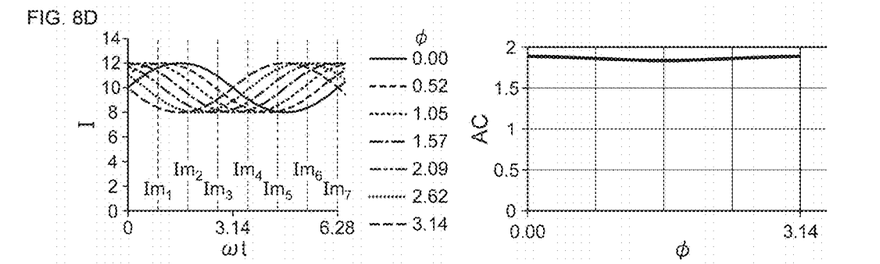

FIG. 8D is a waveform diagram showing a case in which M=7. The calculation value of the AC value, the ideal value of which is 2, becomes 1.87±0.10. This means that such an arrangement leads to a reduction in sensitivity to 93% with a relative error of 1%. In a case in which such a reduction in sensitivity is allowable, by calculating the AC value multiple times with random phase differences $\phi$, such an arrangement provides the AC value with sufficiently small error.

Also, an arrangement may be made in which M is set to a value other than the aforementioned values so as to provide similar results, which can be clearly understood by those skilled in this art. Also, the conversion Expressions for M=3, 5, 6, and 7, are not restricted to such arrangements described above for exemplary purposes only. Such conversion Expressions can be generalized as follows.

$$I_1=\Sigma_{i=1\ to\ M}(K_{1i}\times Im_i)$$

$$I_2=\Sigma_{i=1\ to\ M}(K_{2i}\times Im_i)$$

$$I_3=\Sigma_{i=1\ to\ M}(K_{3i}\times Im_i)$$

$$I_4=\Sigma_{i=1\ to\ M}(K_{4i}\times Im_i)$$

$$\Sigma_{j=1\ to\ 4}K_{ji}=1\ (i=1,2,\ldots,M)$$

By optimizing the coefficients $K_{ji}$, such an arrangement has the potential to provide higher-precision measurement as compared with the aforementioned examples.

By generalizing the conversion Expression in a case in which N≠4, the following Expressions can be obtained.

$$I_j=\Sigma_{i=1\ to\ M}(K_{ji}\times Im_i)\ (j=1,2,\ldots,N)$$

$$\Sigma_{j=1\ to\ N}K_{ji}=C\ (i=1,2,\ldots,M)$$

Here, C represents a given constant. Description has been made in the aforementioned examples in a case in which C=1.

[Results of Investigation With Respect to the DC Value and the AC Value]

Description will be made in a case in which the waveform is represented by the following Expression (A).

$$I(\omega t)=DC+AC\times\sin(\omega t+\phi) \quad \text{(A)}$$

Here, $\omega$ represents the angular frequency, t represents time, and $\phi$ represents a given phase.

A given period ($0\leq\omega t\leq 2\pi$) is divided into four sections. The waveform is integrated for every section. In this case, the following Expressions are obtained.

$$I_1=\int_{0\ to\ \pi/2}I(\omega t)dt$$

$$I_2=\int_{\pi/2\ to\ \pi}I(\omega t)dt$$

$$I_3=\int_{\pi\ to\ 3\pi/2}I(\omega t)dt$$

$$I_4=\int_{3\pi/2\ to\ 2\pi}I(\omega t)dt$$

Mathematically, the DC value and the AC value are calculated as represented by the following Expressions.

$$DC=(I_1+I_2+I_3+I_4)/4\times 2/\pi \quad \text{(B)}$$

$$AC=\sqrt{\{(I_1-I_3)^2+(I_2-I_4)^2\}}/(2\sqrt{2}) \quad \text{(C)}$$

Figure 9A:
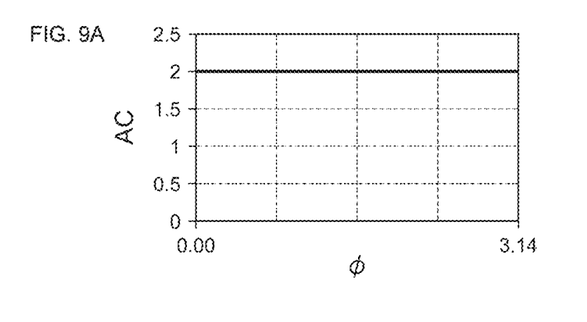
FIGS. 9A through 9D are diagrams showing the relations between the phase $\phi$ and the AC value calculated using different waveforms I($\omega$t).

FIGS. 9A through 9D are diagrams showing relations between the phase $\phi$ and the AC value calculated based on the Expression (C) with different waveforms $I(\omega t)$. FIG. 9A shows an example in a case of employing a sine wave with a DC value of 10 and an AC value of 2. The AC value as represented by the Expression (C) does not depend on the phase $\phi$. This is a mathematical reason why the Expressions (3) and (4) hold true regardless of the phase difference of the driving signal S1.

Figure 9B:
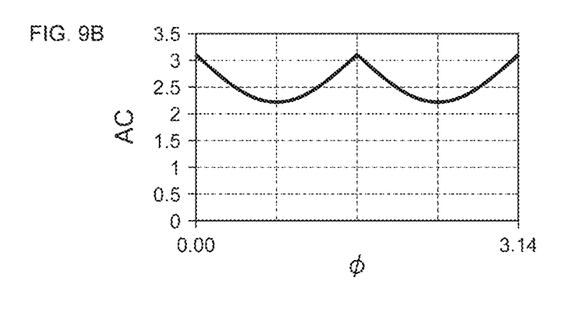

FIG. 9B shows an example in a case in which $I(\omega t)$ represents a rectangular wave.

$$I(\omega t-\phi)=8\ (1<\omega t\leq\pi)$$

$$I(\omega t-\phi)=12\ (\pi<\omega t<2\pi)$$

In a case of employing such a rectangular wave, the AC value calculated based on Expression (C) becomes a value ranging between 2.23 and 3.11, which depends on the phase $\phi$, with a maximum systematic error of 11.7%. Here, the systematic error represents error involved in a single measurement. By calculating the AC value multiple times with random phase differences $\phi$ so as to provide an average value, such an arrangement provides the AC value with high precision. In a case of employing the driving signal S1 having such a rectangular wave, such an arrangement leads to a reduction in precision as compared with an arrangement employing a sine wave. However, such an arrangement provides an advantage of allowing the operation of the light polarization analyzer 1 to be controlled in a simple manner.

Figure 9C:
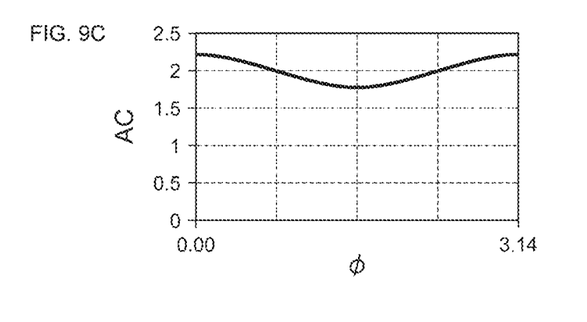

FIG. 9C shows an example in a case in which $I(\omega t)$ is a waveform that approximates a sawtooth wave.

$$I(\omega t)=DC+AC\times[\sin(\omega t+\phi)+\tfrac{1}{2}\cdot\sin 2(\omega t+\phi)+\tfrac{1}{3}\cdot\sin 3(\omega t+\phi)]$$

That is to say, $I(\omega t)$ is configured as a waveform obtained by subjecting a given sawtooth wave to Fourier series expansion, and by making an approximation using only the terms $\omega$, $2\omega$, and $3\omega$ without the fourth and subsequent terms. In this case, the AC value becomes a value ranging between 1.78 and 2.22, which depends on the phase $\phi$, with a maximum systematic error of 7.8% according to the phase φ. By calculating an average value of the AC values acquired multiple times with random phases φ, such an arrangement allows such a systematic error to be handled as accidental error.

Figure 9D:
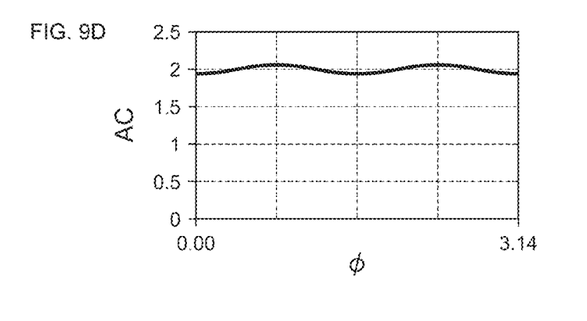

FIG. 9D shows an example in a case in which I(ωt) is a waveform that approximates a triangle wave.

$$I(\omega t) = DC + AC \times X$$

$$X = \sin(\omega t + \phi) - \tfrac{1}{9}\sin 3(\omega t + \phi) + \tfrac{1}{25}\sin 5(\omega t + \phi) - \tfrac{1}{81}\sin 9(\omega t + \phi)$$

In this case, the AC value becomes a value ranging between 1.94 and 2.05, which depends on the phase φ, with a maximum systematic error of 2.1%. By calculating an average value of the AC values acquired multiple times with random phases φ, such an arrangement allows such a systematic error to be handled as accidental error.

As described above, it can be mathematically understood that, in addition to a sine wave, other kinds of waveforms can be employed as the waveform of the driving signal S1.

While the preferred embodiments of the present invention have been described using specific terms, such description is for illustrative purposes only, and it is to be understood that changes and variations may be made without departing from the spirit or scope of the appended claims.

The invention claimed is:

1. A light polarization analyzer comprising:
    an excitation light source that emits an excitation light polarized in a predetermined direction to a sample to be measured;
    an image sensor comprising a plurality of pixels arranged in a one-dimensional manner or otherwise a two-dimensional manner so as to receive a measurement light generated from the sample in response to the excitation light;
    a polarization selector that is arranged between the sample and the image sensor, that comprises a plurality of pixels arranged in a one-dimensional manner or otherwise a two-dimensional manner, and that is configured such that each pixel receives a corresponding portion of the measurement light, selects the measurement light having a polarization direction that corresponds to a driving signal applied to the pixel, and supplies the selected measurement light to the image sensor; and
    a measurement control unit that supplies the driving signal configured as a cyclic signal having a first period $T_1$ to each pixel of the polarization selector, and that acquires data $I_1$ through $I_N$ that represent values obtained by integration, addition, or accumulation of the input light input to each pixel of the image sensor for exposure time segments $T_{2\_1}$ through $T_{2\_N}$, each of which have an exposure period $T_2 = T_1/N$ obtained by dividing the first period $T_1$ by N (N represents a plural integer),
    wherein the light polarization analyzer measures a polarization state of a corresponding portion of the measurement light for each pixel based on the corresponding data $I_1$ through $I_N$ acquired for the corresponding pixel of the image sensor.

2. The light polarization analyzer according to claim 1, wherein N=4, and data $I_1$ through $I_4$ are acquired.

3. The light polarization analyzer according to claim 2, wherein the measurement control unit calculates $\sqrt{\{(I_1-I_3)^2+(I_2-I_4)^2\}}/(I_1+I_2+I_3+I_4)$ for every pixel, so as to measure a polarization degree P.

4. The light polarization analyzer according to claim 1, wherein the measurement control unit acquires intermediate data $Im_1$ through $Im_M$ from each pixel of the image sensor for exposure time segments $T_{3\_1}$ through $T_{3\_M}$, each of which have an exposure period $T_3 = T_1/M$ obtained by dividing the first period $T_1$ by a plural number, i.e., M (M≥3, M≠N),
    and wherein the measurement control unit converts the intermediate data $Im_1$ through $Im_M$ into the data $I_1$ through $I_N$.

5. The light polarization analyzer according to claim 1, wherein the polarization selector comprises:
    a liquid crystal panel; and
    a polarizer.

6. The light polarization analyzer according to claim 1, wherein the driving signal has any one waveform from among a sine wave, a rectangular wave, a sawtooth wave, and a trapezoidal wave.

* * * * *